United States Patent
Tsuda et al.

[11] Patent Number: 5,324,873
[45] Date of Patent: Jun. 28, 1994

[54] AZEOTROPIC MIXTURE OF HYDROGEN FLUORIDE AND 1,1,1-TRIFLUORO-2-CHLOROETHANE AND PROCESS FOR PURIFICATION OF 1,1,1-TRIFLUORO-2-CHLOROETHANE

[75] Inventors: Takehide Tsuda; Nobuyoshi Iwashita; Satoshi Komatsu; Satoshi Koyama, all of Settsu, Japan

[73] Assignee: Daikin Industries Limited, Osaka, Japan

[21] Appl. No.: 17,258

[22] Filed: Feb. 12, 1993

Related U.S. Application Data

[62] Division of Ser. No. 868,209, Apr. 14, 1992.

[30] Foreign Application Priority Data

Apr. 15, 1991 [JP] Japan .................... 3-82261

[51] Int. Cl.⁵ .................................... C07C 17/38
[52] U.S. Cl. .................................... 570/178; 570/123; 570/161; 570/177
[58] Field of Search .............. 570/123, 124, 134, 161, 570/177, 178

[56] References Cited

U.S. PATENT DOCUMENTS

| | | | |
|---|---|---|---|
| 2,450,415 | 10/1948 | Benning | 570/178 |
| 3,003,003 | 10/1961 | McGinty | 570/167 |
| 3,406,099 | 10/1968 | Buckman et al. | 570/178 |
| 3,873,629 | 3/1975 | Jones | 570/178 |
| 3,947,558 | 3/1976 | van Eijil | 570/178 |
| 4,024,086 | 5/1977 | Hutchinson | 252/162 |
| 4,057,974 | 11/1977 | Murphy et al. | 62/114 |
| 4,101,436 | 7/1978 | Murphy et al. | 252/67 |
| 4,129,603 | 12/1978 | Bell | 570/178 |
| 4,209,470 | 6/1980 | Lorquet | 570/178 |
| 4,885,416 | 12/1989 | Mader | 570/170 |
| 4,911,792 | 3/1990 | Manzer et al. | 570/178 |
| 4,944,846 | 7/1990 | Manzer et al. | 570/178 |
| 5,094,773 | 3/1992 | Manzer et al. | 570/178 |
| 5,196,616 | 3/1993 | Lee et al. | 568/178 |

FOREIGN PATENT DOCUMENTS

| | | |
|---|---|---|
| 0353970 | 2/1990 | European Pat. Off. . |
| 0354697 | 2/1990 | European Pat. Off. . |
| 462514 | 12/1991 | European Pat. Off. . |
| 1585938 | 3/1981 | United Kingdom . |
| 91/04955 | 4/1991 | World Int. Prop. O. ......... 570/177 |
| 0004955 | 4/1991 | World Int. Prop. O. ......... 570/178 |

Primary Examiner—Werren B. Lone
Attorney, Agent, or Firm—Birch, Stewart, Kolasch & Birch

[57] ABSTRACT

Hydrogen fluoride and 1,1,1-trifluoro-2-chloroethane forms an azeotropic mixture. A mixture comprising hydrogen fluoride and 1,1,1-trifluoro-2-chloroethane is phase separated when it is cooled to a temperature below 7° C. 1,1,1-Trifluoro-2-chloroethane is purified effectively from the mixture by cooling the mixture to form an upper liquid phase and a lower liquid phase and distilling the lower liquid phase so that the hydrogen fluoride is removed as an azeotropic distillate and 1,1,1-trifluoro-2-chloroethane substantially free from hydrogen fluoride is obtained as a bottom product.

12 Claims, 1 Drawing Sheet

5,324,873

AZEOTROPIC MIXTURE OF HYDROGEN FLUORIDE AND 1,1,1-TRIFLUORO-2-CHLOROETHANE AND PROCESS FOR PURIFICATION OF 1,1,1-TRIFLUORO-2-CHLOROETHANE

This application is a divisional of copending application Ser. No. 07/868,209, filed on Apr. 14, 1992, the entire contents of which are hereby incorporated by reference.

BACKGROUND OF THE INVENTION

1. Field of the Invention

The present invention relates to an azeotropic mixture of hydrogen fluoride (hereinafter referred to as "HF") and 1,1,1-trifluoro-2-chloroethane (hereinafter referred to as "R-133a") and a process for the purification of R-133a by removing HF from a mixture comprising HF and R-133a. R-133a is of interest since it is one representative cooling medium which can replace dichlorodifluoromethane. Also R-133a is a suitable raw material of HFC-134a (1,1,1,2-tetrafluoroethane) and it is a suitable raw material of trifluoroethanol.

2. Description of the Related Art

R-133a is generally produced by reacting a carbon chloride such as trichloroethylene with HF. HF is removed from a reaction mixture comprising HF and R-133a as main components by washing the mixture with an aqueous solution. This technique is undesirable since a large amount of alkali is required to neutralize the washing solution.

SUMMARY OF THE INVENTION

We found that a mixture comprising HF and R-133a as main components separate into two liquid phases, that is, an upper liquid phase rich in HF and a lower liquid phase rich in R-133a (a ratio HF/R-133a of the lower liquid phase is smaller than that of the original mixture before the liquid separation) when it is cooled to a temperature below 7° C., and that HF and R-133a forms an azeotropic mixture having a minimum boiling point. The azeotropic mixture can be used as a reflux during a distillation process in which HF and/or R-133a are separated from a mixture comprising the both, so that efficient separation can be carried out.

In the first aspect, the present invention provides an azeotropic mixture having a minimum boiling point which consists essentially of HF and R-133a. The boiling point of the azeotropic mixture is about −2° C. at an atmospheric pressure.

In the second aspect, the present invention provides a process for the purification of one component of HF and R-133a by cooling a mixture comprising HF and R-133a as main components to a temperature below 7° C. to separate it into an upper liquid phase rich in HF and a lower liquid phase rich in R-133a, and treating either liquid phase by a proper unit operation, for example distillation, adsorption, absorption and combination thereof, to remove preferentially the other component so that the one component is concentrated relative to the other component and preferably substantially separated from the other component. The purification by concentrating one component herein means that a concentration of the one component of a mixture comprising two components is increased relative to a concentration of the other component of the mixture.

In the third aspect, the present invention provide a process for the purification of HF or R-133a by distilling a mixture comprising HF and R-133a as main components, preferably the upper liquid phase rich in HF or the lower liquid phase rich in R-133a which may be obtained by the process according to the second aspect of the present invention so that an azeotropic mixture comprising HF and R-133a is removed and HF or R-133a substantially free from R-133a or HF is obtained.

DETAILED DESCRIPTION OF THE INVENTION

Figure 1:
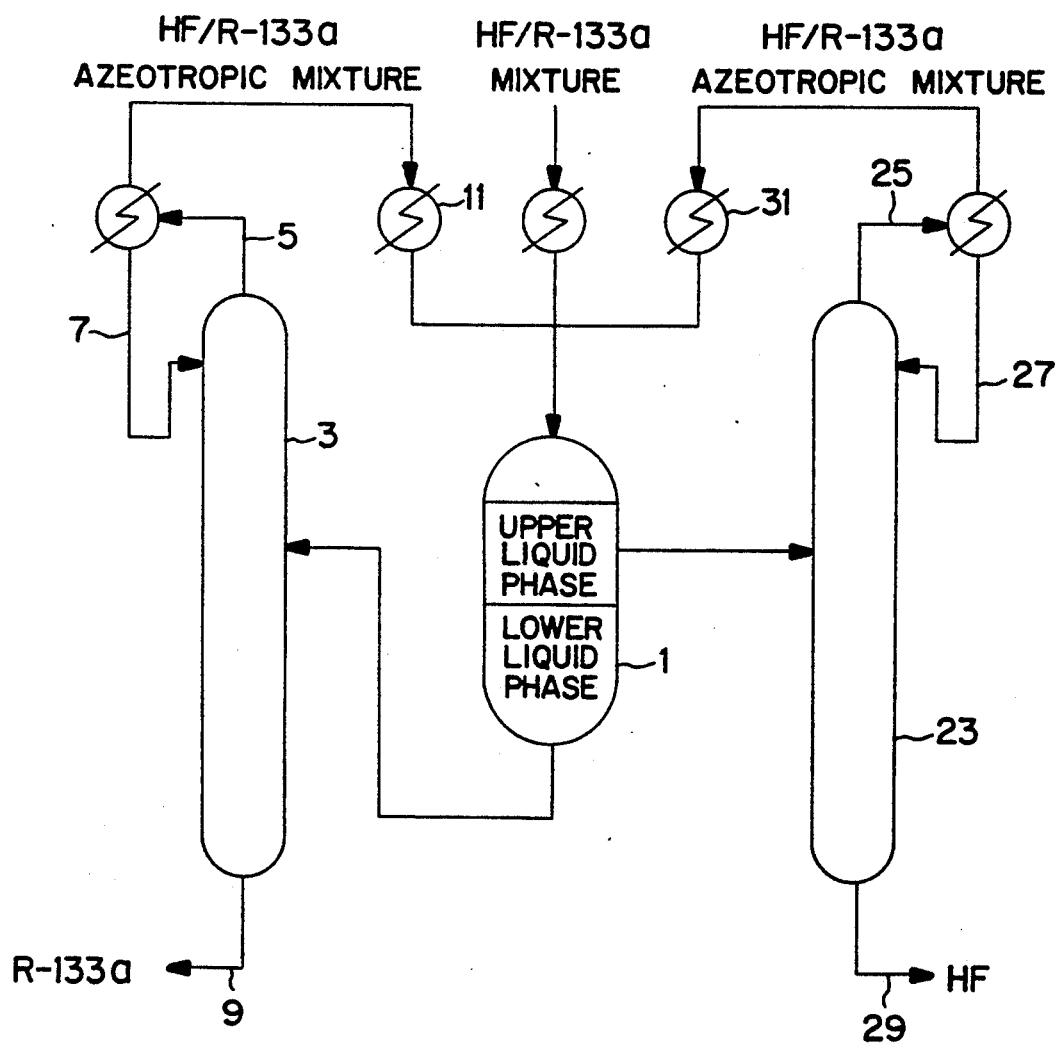
FIG. 1 shows a process flow sheet of one preferred embodiment in which the present purification process is carried out.

As described above, a two component system comprising HF and R-133a has the azeotropic mixture having the minimum boiling point, which azeotropic mixture has been found by us for the first time. When the mixture comprising HF and R-133a as the main components is distilled at an atmospheric pressure, no further concentration of HF from a molar ratio HF/R-133a of about 65/35 is possible. In other words, at such a molar ratio, composition of a liquid phase is the same as that of a vapor phase which is equilibrium with the liquid phase. The molar ratio HF/R-133a of the azeotropic mixture of the present invention changes with a system pressure. For example, when the system pressures are 1.5 Kg/cm$^2$G, 4.0 Kg/cm$^2$G and 15 Kg/cm$^2$G, the molar ratios (HF/R-133a) are about 60/40, about 55/45 and about 45/55, respectively.

In addition, after cooling the mixture comprising HF and R-133a and the separation into the two phases, a concentration of R-133a of the lower liquid phase is increased compared with that before the cooling. It has been found that when increased, a R-133a concentration of the lower liquid phase is deviated into a R-133a concentration greater than that of the azeotropic mixture.

Cooling the mixture comprising HF and R-133a produces the lower liquid phase rich in R-133a and the upper liquid phase rich in HF. Merely cooling the mixture provides the upper liquid phase and the lower liquid phase each of which is rich in either component compared with the original mixture before the cooling. The concentration of R-133a in the lower liquid phase may be further increased when the obtained lower liquid phase is subjected to any proper treatment such as distillation, extraction, absorption, adsorption or neutralization with an alkali in which HF is preferentially removed so that R-133a is concentrated and purified.

Since the upper liquid phase is rich in HF, it is subjected to any proper treatment in which R-133a is preferentially removed as in the case of the treatment of the lower liquid phase so that HF is concentrated and purified. Thus, merely cooling facilitates the first rough separation step.

A temperature at which the mixture is cooled (cooling temperature) is usually below 7° C. The mixture may not be liquid-separated at a temperature above 7° C. at any ratio of HF/R-133a. The preferred cooling temperature is below 5° C. At a temperature above 5° C., a composition of the upper liquid phase is not so different from that of the lower liquid phase, so that a density of the upper liquid phase is also not so different from that of the lower liquid phase, which may make the liquid separation insufficient. There is no specific lower limitation of the cooling temperature, provided that the temperature is higher than a solidifying point of R-133a (about −100° C.). Generally, the cooling temperature is preferably above about −50° C. Operation at a temperature below −50° C. is uneconomical since much energy is required for the cooling. The cooling temperature is more preferably in the range of −20° C. to 0° C.

HF may be separated from the mixture comprising R-133a and HF by directly distilling the mixture with the use of any type of a distillation apparatus. On such distillation, the azeotrope mixture of HF and R-133a is used as a reflux and returned to the distillation apparatus during the distillation operation so that a distillate of the azeotropic mixture is efficiently obtained from the top of the distillation apparatus, and R-133a substantially free from HF is obtained from the bottom of the apparatus when the concentration of R-133a of the mixture fed into the apparatus is deviated into the R-133a concentration greater than that of the azeotropic mixture.

The azeotropic distillation apparatus may be any type of a distillation apparatus which has conventional means necessary for the usual distillation operation. For example, a distillation column having trays or a packed column may be preferably used. The azeotropic distillation may be carried out in a continuous operation or in a batch operation.

In a preferred embodiment of the present invention, the mixture comprising HF and R-133a is cooled so that the mixture is divided into the upper liquid phase rich in HF and the lower liquid phase rich in R-133a, and then each liquid phase is subjected to the azeotropic distillation separately. The upper liquid phase is divided into a distillate of the azeotropic mixture of R-133a and HF distilled from the top of the distillation apparatus and the rest of HF substantially free from R-133a withdrawn as a bottom product from the apparatus, provided that the HF concentration of the upper liquid phase is deviated into a HF concentration which is greater than that of the HF concentration of the azeotropic mixture. Since the R-133a concentration of the lower liquid phase is deviated into the R-133a concentration which is larger than that of the azeotropic mixture, the lower liquid phase is divided into a distillate of the azeotrope mixture of R-133a and HF distilled from the top of the other distillation apparatus and the rest of R-133a substantially free from HF withdrawn as a bottom product from the apparatus.

The present invention is useful for the removal of HF from a mixture produced in a reaction of trichloroethylene with HF in a liquid phase or in a vapor phase in the presence of a catalyst. One preferred embodiment of the present invention will be explained below.

FIG. 1 shows a flow sheet of one example of preferred purification plants which may be used in the present invention. Usually the mixture obtained from the reaction is withdrawn in the form of a gaseous phase. The mixture comprises R-133a, HF and hydrogen chloride in addition to small amounts of organic substances. Hydrogen chloride is removed from the mixture by distillation. Then, the mixture is cooled to a temperature below 7° C., preferably below 5° C., more preferably below 0° C. through a cooler and passed to a liquid phase separation device 1 such as a decanter to form the two liquid phases. There is R-133a substantially free from HF at the bottom of the distillation apparatus 3, which may be withdrawn as a bottom product.

On one hand, the lower liquid phase rich in P-133a from the separation device 1 is supplied to a distillation apparatus 3 and an azeotropic mixture 5 is distilled from the top of the apparatus 3. During such distillation, a portion of the distilled azeotropic mixture is returned, as a reflux, to the top of the apparatus 3. The rest of the distillate is passed to the liquid separation device 1 after cooled to a temperature below 7° C. at a cooler 11 and then above procedures are repeated. There remains R-133a substantially free from HF at the bottom of the distillation apparatus 3, which is withdrawn as a bottom product 9.

On the other hand, the upper liquid phase rich in HF in the liquid separation device 1 may be returned to any reaction system, if possible. Alternatively, it may be distilled in the other distillation apparatus. In FIG. 1, the upper liquid phase is supplied to another distillation apparatus 23 where it is divided into an azeotropic distillate 2 of HF and R-133a and a bottom product 29 of HF substantially free from R-133a. A portion of the distillate is returned, as a reflux 27, to the top of the distillation apparatus 23 as in the case of distillation apparatus 3. The rest of the distillate is cooled to a temperature below 7° C. at a cooler 31 and then returned to the liquid separation device 1. The bottom product 29 substantially free from R-133a may be reused.

As described above, all HF is utilized while R-133a is purified. These procedures may be carried out in a continuous or a batch mode.

The present invention will be further explained with reference to some Examples below.

EXAMPLE 1

HF (40 g, 2.0 mol) and R-133a (592.5 g, 5.0 mol) were charged into an evacuated packed column (diameter: 25 mm, packing: McMahon packing, effective packing height: 1500 mm) made of stainless steel. Distillation was started from a total reflux condition and a temperature of the still (bottom) was raised gradually. When the pressure at the top of the column came to 1.5 Kg/cm$^2$G and the temperature at the top came to 19° C., a first sample was obtained from a reflux line. The first sample was analyzed on the molar ratio HF/R-133a and the ratio was found to be 58/42.

The temperature of the still was raised again at the total reflux condition, and a second sample was obtained from the reflux line when the top pressure and the temperature came to 4.0 Kg/cm$^2$G and 40° C., respectively. The molar ratio of HF/R-133a of the second sample was 55/45.

From these results, HF having its normal boiling point of 19° C. higher than that of R-133a of 7° C. is concentrated toward the top of the distillation apparatus, which means that R-133a and HF form the azeotrope mixture.

EXAMPLE 2

A mixture (60 g) having the same composition as that of the mixture of the first sample of Example 1 was charged in an evacuated vapor-liquid equilibrium measuring apparatus made of stainless steel (effective volume of which was 75 ml) and heated the whole apparatus so that a system pressure came to 1.5 Kg/cm$^2$G. After the reached an equilibrium state, samples were obtained from a liquid phase and a vapor phase. (The sample from the vapor phase was obtained in the form of liquid after condensation of the vapor phase.) As to the second sample in Example 1, the same procedures were repeated as in the case of the first sample except that the system pressure was changed.

HF concentrations of the samples of each phase are shown in Table 1. The concentration of R-133a is the balance.

TABLE 1

| Sample | HF concentration (mol %) | | Pressure Kg/cm²G | Temperature °C. |
|---|---|---|---|---|
| | Liquid Phase | Vapor Phase | | |
| 1 | 58 | 59 | 1.5 | 20 |
| 2 | 55 | 55 | 4.0 | 41 |

Clearly seen from the above data, the composition of the liquid phase is substantially equal to that of the vapor phase, each within an experimental error, and HF and R-133a form the azeotropic mixture.

EXAMPLE 3

HF and R-133a were charged into an evacuated vessel made of a fluorine plastic at a molar ratio HF/R-133a of 60/40 and then mixed together. The mixture was settled at 0° C. to be phase-separated. The molar ratio HF/R-133a of the separated lower liquid phase was measured and found to be 30/70. The molar ratio HF/R-133a of the upper liquid phase was also measured and found to be 84/16.

EXAMPLES 4–6

Example 3 was repeated except that the phase separation temperature was changed. The separation temperatures and the molar ratio HF/R-133a of the lower phases are shown in Table 2 together with the results of Example 3.

TABLE 2

| Example | Sep. Temp. | HF/R-133a Ratio (lower phase) |
|---|---|---|
| 3 | 0° C. | 30/70 |
| 4 | −5° C. | 20/80 |
| 5 | −10° C. | 10/90 |
| 6 | 5° C. | 50/50 |

Note: Before the phase separation, the molar ratio HF/R-133a was 60/40.

It is understood that the molar ratio HF/R-133a of the lower liquid phase is remarkably reduced after the phase separation.

EXAMPLE 7

HF (150 g, 7.5 mol) and R-133a (592.5 g, 5.0 mol) were charged into an evacuated vessel made of the fluorine plastic (effective volume 1000 ml) and cooled to −20° C. After the cooling the mixture of HF and R-133a was phase-separated into a lower liquid phase and an upper liquid phase, and the lower phase was recovered which contained 1 g of HF (0.05 mol) and 435.5 g of R-133a (3.68 mol). Thus, the molar ratio HF/R-133a was 1.34/98.66, and the concentration of R-133a was greatly deviated into the R-133a concentration which is greater than that of the azeotropic mixture.

The recovered lower liquid phase (400 g) was charged in the same distillation column as used in Example 1 made of stainless steel and a temperature of a column still was gradually raised at a total reflux condition. When the top pressure of the column came to 1.5 Kg/cm²G and the top temperature of the column came to 20° C., a first distilled sample was obtained (2 g) from the top of the column (reflux line), which was analyzed on its HF/R-133a ratio. The molar ratio was found to be 60.8/39.2.

The still temperature was further raised until the top pressure and the top temperature came to 4.0 Kg/cm²G and 41° C., respectively. Then, another distillate sample was obtained (2 g). The molar ratio HF/R-133a of the second sample was found to be 56.6/43.4.

The system pressure was adjusted to 1.5 Kg/cm²G, again and the distillation column was stabilized at the total reflux condition. After the stabilization, when a distillate was withdrawn from the top of the column little by little, the top temperature started to rise. When the top temperature became equal to the still temperature, heating was stopped. A total amount of the distillate withdrawn from the top was 20 g (including amounts of the samples on the way) and about 380 g of R-133a containing about 10 ppm of HF was obtained as the bottom product from the still.

EXAMPLE 8

HF (150 g, 7.5 mol) and R-133a (592.5 g, 5.0 mol) were charged into an evacuated vessel made of the fluorine plastic (effective volume 1000 ml) and cooled to −20° C. After the cooling the mixture of HF and R-133a was liquid-separated into a lower liquid phase and an upper liquid phase, and the upper phase was recovered which contained 149 g of HF (7.45 mol) and 157 g of R-133a (1.32 mol). Thus, the molar ratio HF/R-133a was 84.95/15.05, and the concentration of HF was greatly deviated into the HF concentration which is larger than that of the azeotropic mixture.

The recovered upper liquid phase (300 g) was charged in the same distillation column made of stainless steel as used in Example 1 and the temperature of the column still was gradually raised at the total reflux condition. When the top pressure of the column came to 1.5 Kg/cm²G and the top temperature of the column came to 20° C., a first distillate sample was obtained (2 g) from the reflux line, which was analyzed on its HF/R-133a ratio. The molar ratio was found to be 59.5/40.5.

The still temperature was further raised until the top pressure and the top temperature became 4.0 Kg/cm²G and 40° C., respectively. Then, another distillate sample was obtained (2 g). The molar ratio HF/R-133a was found to be 57.5/42.5.

The system pressure was adjusted to 1.5 Kg/cm²G, again and the distillation column was stabilized at the total reflux condition. After the stabilization, when distillate was withdrawn from the top of the column little by little, the top temperature started to rise. When the top temperature became equal to the still temperature, heating was stopped. A total amount of the distillate withdrawn from the top was about 240 g (including amounts of the samples on the way) and about 60 g of HF containing a trace amount of R-133a was obtained as the bottom product from the still.

What is claimed is:
1. A process for the purification of 1,1,1-trifluoro-2-chloroethane which comprises step of
 cooling a mixture comprising hydrogen fluoride and 1,1,1-trifluoro-2-chloroethane to a temperature below 7° C., liquid-separating the mixture into an upper liquid
phase rich in hydrogen fluoride and a lower liquid
phase rich in 1,1,1-trifluoro-2-chloroethane, and
recovering 1,1,1-trifluoro-2-chloroethane containing
less amount of hydrogen fluoride from the lower
liquid phase.

2. The process for the purification according to claim
1 in which the mixture is cooled to a temperature below
5° C.

3. The process according to claim 1 wherein the
mixture comprising hydrogen fluoride and 1,1,1-trifluoro-2-chloroethane is a mixture produced in a reaction of trichloroethylene with hydrogen fluoride.

4. A process for the purification of 1,1,1-trifluoro-2-chloroethane which comprises a step of distilling a mixture comprising hydrogen fluoride and 1,1,1-trifluoro-2-chloroethane so that hydrogen fluoride is removed as an azeotropic mixture consisting essentially of hydrogen fluoride and 1,1,1-trifluoro-2-chloroethane.

5. The process according to claim 4 wherein the mixture comprising hydrogen fluoride and 1,1,1-trifluoro-2-chloroethane is a mixture produced in a reaction of trichloroethylene with hydrogen fluoride.

6. A process for the purification of 1,1,1-trifluoro-2-chloroethane which comprises steps of
cooling a mixture comprising hydrogen fluoride and 1,1,1-trifluoro-2-chloroethane to a temperature below 7° C.,
liquid-separating the mixture into an upper liquid phase rich in hydrogen fluoride and a lower liquid phase rich in 1,1,1-trifluoro-2-chloroethane, and
distilling the lower liquid phase rich in 1,1,1-trifluoro-2-chloroethane so that hydrogen fluoride is removed as an azeotropic distillate consisting essentially of hydrogen fluoride and 1,1,1-trifluoro-2-chloroethane.

7. The process for the purification according to claim 6 in which the mixture is cooled to a temperature below 5° C.

8. The process for the purification according to claim 6 in which the azeotropic mixture from the distilling step is returned to the cooling step.

9. The process for the purification according to claim 8 in which the mixture is cooled to a temperature below 5° C.

10. The process according to claim 6 wherein the mixture comprising hydrogen fluoride and 1,1,1-trifluoro-2-chloroethane is a mixture produced in a reaction of trichloroethylene with hydrogen fluoride.

11. A process for the purification of 1,1,1-trifluoro-2-chloroethane which comprises steps of
cooling a mixture comprising hydrogen fluoride and 1,1,1-trifluoro-2-chloroethane to a temperature below 7° C.,
liquid-separating the mixture into an upper liquid phase rich in hydrogen fluoride and a lower liquid phase rich in 1,1,1-trifluoro-2-chloroethane,
distilling the upper liquid phase so that 1,1,1-trifluoro-2-chloroethane is recovered as an azeotropic distillate consisting essentially of hydrogen fluoride and 1,1,1-trifluoro-2-chloroethane,
distilling the lower liquid phase so that hydrogen fluoride is recovered as an azeotropic distillate consisting essentially of hydrogen fluoride and 1,1,1-trifluoro-2chloroethane and 1,1,1-trifluoro-2-chloroethane substantially free from hydrogen fluoride is recovered as a bottom product, and
recycling the distillates from the two distilling steps to the cooling step.

12. The process according to claim 11 wherein the mixture comprising hydrogen fluoride and 1,1,1-trifluoro-2-chloroethane is a mixture produced in a reaction of trichloroethylene with hydrogen fluoride.

* * * * *